United States Patent [19]

Creuzet et al.

[11] Patent Number: 4,600,788

[45] Date of Patent: Jul. 15, 1986

[54] 4'-FLAVONECARBOXYLIC ACIDS AND PHARMACEUTICALLY ACCEPTABLE DERIVATIVES THEIR PREPARATION, AND THEIR APPLICATION

[75] Inventors: Marie-Hélène Creuzet, Bordeaux; Claude Feniou, Pessac; Francoise Guichard, Bordeaux; Gisèle Prat, Talence; Jacqueline Mosser, Saint-Medard-en-Jalles; Henri Pontagnier, Pessac, all of France

[73] Assignee: Societe Cortial, S.A., Paris, France

[21] Appl. No.: 592,272

[22] Filed: Mar. 22, 1984

[30] Foreign Application Priority Data

Mar. 24, 1983 [FR] France ............... 83 05013

[51] Int. Cl.⁴ .................................. C07D 311/04
[52] U.S. Cl. .................................. 549/403
[58] Field of Search ................. 549/400, 401, 403

[56] References Cited

U.S. PATENT DOCUMENTS 4,352,792 10/1982 Ishitsuka et al. ............... 424/180

FOREIGN PATENT DOCUMENTS 1057349 2/1967 United Kingdom ............... 200/

Primary Examiner—Ethel G. Love
Attorney, Agent, or Firm—Oblon, Fisher, Spivak, McClelland & Maier

[57] ABSTRACT

This invention relates to new products of the general formula

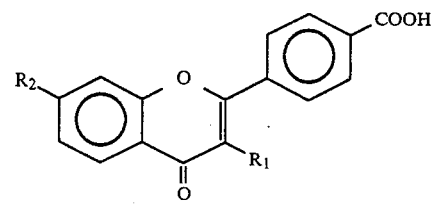

where $R_1$ = H, OH, OCOCH$_3$, OSO$_2$CH$_3$, branched or unbranched alkyl containing 1 to 5 carbon atoms. $R_2$ = NHCOR$_3$, NHCOCH$_2$X, NHSO$_2$CH$_3$, N(SO$_2$CH$_3$)$_2$, SO$_2$N(CH$_3$)$_2$, SO$_2$NHCH$_3$, SO$_2$NCH$_3$CH$_2$CH$_2$OH, SO$_2$NH$_2$ wherein $R_3$ is a lower alkyl containing 1 to 4 carbon atoms; and X is NR$_4$R$_5$ or

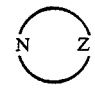

wherein $R_4$ and $R_5$ are both independently lower alkyls containing 1 to 4 carbon atoms and

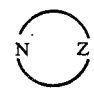

is piperidine, pyrrolidine or morpholine. These products can be in the form of pharmaceutically acceptable derivatives such as esters, amides, salts. When $R_2$ contains an amino function, the product can be in the form of an acid salt.

These products are prepared from their methyl esters either by reaction between

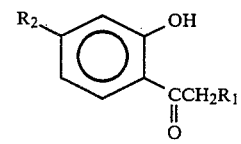

and paramethoxycarbonylbenzoic acid chloride or by means of derivative I such as $R_2$ is NH$_2$.

The products of this invention are used in therapy in the prevention and treatment of complications from diabetes or as diuretics.

6 Claims, No Drawings

4'-FLAVONECARBOXYLIC ACIDS AND PHARMACEUTICALLY ACCEPTABLE DERIVATIVES THEIR PREPARATION, AND THEIR APPLICATION

BACKGROUND OF THE INVENTION

4'-Flavonecarboxylic acid derivatives are already known. In particular, the Soci/été Fisons filed a Belgian Pat. No. 815896 on June 4, 1974, describing in particular 4'-flavonecarboxylic acids substituted in the 7 position of the benzopyran ring by radicals such as H, halogen, alkyl, alkoxy, alkenyl, amino, hydroxyl, trifluoromethyl, cyano, alkylamino, alkoxyalkoxy, hydroxylalkoxy or nitro. These products exhibited antianaphylactic activities.

SUMMARY OF THE INVENTION

This invention relates to new 4'-flavonecarboxylic acids and their pharmaceutically acceptable derivatives, the method of preparing them and their application in therapeutics.

The new products, which are the object of this invention, have the general formula:

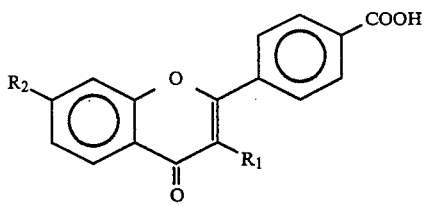

where $R_1$=H, OH, OCOCH$_3$, OSO$_2$CH$_3$, branched or unbranched alkyl containing 1 to 5 carbon atoms $R_2$=NHCOR$_3$, NHCOCH$_2$NR$_4$R$_5$, NHSO$_2$CH$_3$, N(SO$_2$CH$_3$)$_2$, SO$_2$N(CH$_3$)$_2$, SO$_2$NHCH$_3$, SO$_2$NCH$_3$CH$_2$CH$_2$OH, SO$_2$NH$_2$ with $R_3$, $R_4$ and $R_5$=lower alkyl containing 1 to 4 carbon atoms; NR$_4$R$_5$ can also form a heterocycle such as a piperidine, pyrrolidine, or morpholine.

The carboxylic acid radical COOH can be in the form of one of its pharmaceutically acceptable derivatives such as its esters, its amides, its alkali or alkaline-earth metals or its salts of pharmaceutically acceptable organic bases.

In case $R_2$ contains an amino function, the product can be in form of a pharmaceutically acceptable inorganic or organic acid salt.

DESCRIPTION OF THE PREFERRED EMBODIMENTS

We have now discovered that 4'-flavonecarboxylic acids substituted in the 7 position by the groups

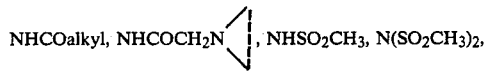

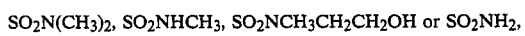

all of which are new chemical products, exhibit aldose reductase inhibitive properties allowing their use in the prevention of the complications, particularly ocular and nervous, of diabetes. These new products are also useful as diuretics.

The formula (I) derivatives are generally prepared from products of the formula

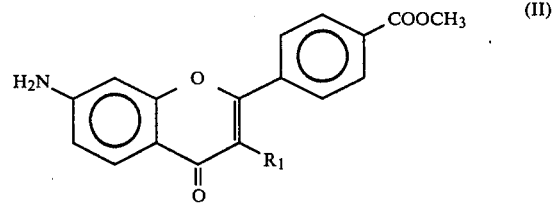

where $R_1$=H, OH, branched or unbranched alkyl containing 1 to 5 carbon atoms.

The formula (II) product such as $R_1$=OH is preferably prepared by a reaction involving 4-acetamido-2-hydroxyacetophenone and terephthalic acid methyl ester leading to a chalcone of the formula

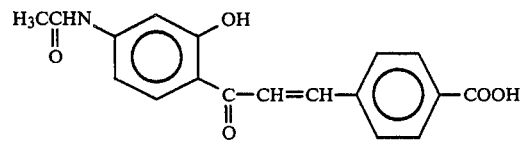

Each chalcone undergoes oxidizing ring closure in an alcohol solvent, such as, for example, ethyl alcohol, in the presence of potassium carbonate and hydrogen peroxide to yield 7-amino-3-hydroxy-4'-flavonecarboxcyclic acid, which is esterified to yield the formula (II) product.

The formula (II) product such as $R_1$=H is preferably prepared from 4-acetamido-2-hydroxyacetophenone and paramethoxycarbonylbenzoic acid chloride by passage through a diketone intermediate that undergoes ring closure in the presence of hydrochloric acid in an alcohol medium such as, for example, methyl alcohol.

The formula (II) products such as $R_1$=branched or unbranched alkyl containing 1 to 5 carbon atoms are preferably prepared by a reaction between a derivative of the formula

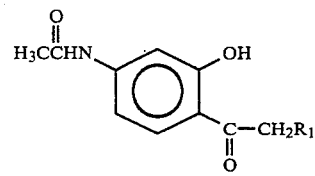

and paramethoxycarbonylbenzoic acid chloride making it possible directly to obtain the methyl esters of formula (I) products with $R_1$=branched or unbranched alkyl containing 1 to 5 carbon atoms and $R_2$=NHCOCH$_3$. The N-deacetylation of the product thus obtained is preferably performed in a solvent such as methyl alcohol in the presence of gaseous hydrochloric acid, although one skilled in the art will easily recognize similar reaction conditions which may also be used.

More generally, the methyl esters of the formula (I) products such as $R_1$=branched or unbranched alkyl containing 1 to 5 carbon atoms and $R_2$=NHCOR$_3$, NHCOCH$_2$NR$_4$R$_5$, NHSO$_2$CH$_3$, N(SO$_2$CH$_3$)$_2$, with $R_3$, $R_4$ and $R_5$=lower alkyl containing 1 to 4 carbon atoms, and NR$_4$R$_5$ also being able to form a heterocycle such as piperidine, pyrrolidine, or morpholine may be obtained directly by a reaction involving a derivative of the formula

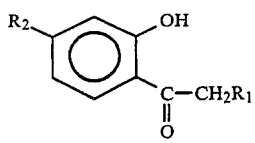

and paramethoxycarbonylbenzoic acid chloride.

The $NH_2$ function of the products of general formula (II) can then be transformed, by standard techniques, into an amide group of carboxylic acid or into a sulfonamide group. This function can also be transformed into a chlorosulfonyl group, which by reaction with amines leads to derivatives such as $R_2=SO_2N(CH_3)_2$, $SO_2NHCH_3$, $SO_2NCH_3CH_2CH_2OH$, or $SO_2NH_2$. In the case the derivative II contains an OH function in $R_1$ it is possible to prepare, by reaction with a carboxylic or sulfonic acid derivative, the methyl esters of formula (I) derivatives such as $R_1=OCOCH_3$ or $OSO_2CH_3$. The acids are obtained from the methyl esters by standard methods of chemistry.

This invention will now be described more precisely in the following examples which are not intended to be limiting of the invention.

EXAMPLE 1

Preparation of 7-acetamido-4'-flavonecarboxylic acid; formula (I) product with $R_1=H$, $R_2=NHCOCH_3$; code name COR19 85

(a) Preparation of 7-amino-4'-flavonecarboxylic acid methyl ester

A mixture consisting of 18 g of 4-acetamido-2-hydroxyacetophenone, 1.7 liters of anhydrous acetone, 100 g of anhydrous potassium carbonate, 22 g of paramethoxycarbonylbenzoic acid chloride are heated with stirring to reflux of the acetone for 10 hours. After cooling and filtering, the filtrate is evaporated. Water is added to the evaporation residue. After acidification, the solid is filtered, washed with water and dried by azeotropy with benzene. Yield 72%. The mixture consisting of 10 g of this diketone thus prepared, 300 ml of methyl alcohol and 300 ml of methyl alcohol saturated with gaseous hydrochloric acid is heated to reflux of the methyl alcohol for an hour. The alcohol is evaporated. Water is added to the evaporation residue. The solution is alkalized and the precipitate is filtered. It is washed with water and dried by azeotropy with benzene. Yield 65%. MP above 260° C.

(b) Preparation of methyl 7-acetamido-4'-flavonecarboxylate

The mixture consisting of 2 g of 7-amino-4'-flavonecarboxylic acid methyl ester thus prepared, 30 cc of pyridine, 15 cc of acetic anhydride is heated at 40° for 2 hours with stirring. Completion of the reaction is verified by thin-layer chromatography (benzene (90)-dioxane (25)-acetic acid (4) elution solvent). The reaction mixture is poured in 500 cc of ice water. The solid that is formed is filtered, washed with water and dried by formation of an azeotropic system with benzene. Yield 56%.

(c) Preparation of 7-acetamido-4'-flavonecarboxylic acid 6 g of 7-acetamido-4'-flavonecarboxylic acid methyl ester are dissolved in 600 cc of dioxane. 12 g of sodium carbonate, dissolved in 250 cc of water, are added and the mixture is heated at 100° C. with stirring until the reaction is complete, for about 8 hours. The reaction is checked by plate chromatography (benzene (90)-dioxane (25)-acetic acid (4) elution solvent).

The reaction mixture is cooled and poured in a liter of ice water. The insoluble material is filtered. The filtrate is acidified to make the acid precipitate. The precipitate is filtered, washed until neutral and dried by azeotropy with benzene. Yield 53%. MP not determinable (decomposition at 240° C.).

NMR in DMSO(D6): chemical shifts in relation to TMS taken as the reference point: $\delta=2.2$ ppm, 3H, singlet, $CH_3$; $\delta=7.0$ ppm, 1H, singlet, H-3; $\delta=7.2-8.5$ ppm, 7H, complex multiplet, aromatic protons; $\delta=10.5$ ppm, 2H, broad peak, COOH+NH; (interchangeable with $D_2O$).

EXAMPLE 2

Preparation of methyl 7-methanesulfonamido-3-methanesulfonyloxy-4'-flavonecarboxylate; formula (I) product with $R_1=OSO_2Me$, $R_2=NHSO_2Me$, methyl ester; code name COR35 07

(a) Preparation of 7-amino-3-hydroxy-4'-flavonecarboxylic acid 38.6 g of 2-acetyl-5-acetamidophenol are dissolved in 600 cc of absolute ethyl alcohol. The mixture is cooled to 0° C. and stirred under argon. 400 cc of 25% alcoholic potash, then 39.2 g of terephthalic acid methyl ester are added. The mixture is allowed to stir for 15 hours at ambient temperature under argon. Ice water is added and it is acidified by acetic acid. The solid is filtered then washed with water. The chalcone is dried in vacuo under $P_2O_5$. Yield 52%. MP >260° C.

8 g of the chalcone are put in suspension in 320 ml of ethyl alcohol. The mixture is stirred and heated at 40° C. 60 ml of 1N KOH are added. The heating bath is removed and 16 cc of 30% hydrogen peroxide are added drop by drop. Stirring is maintained for an hour. 500 cc of ice water are added. The mixture is acidified with dilute sulfuric acid until neutral. The solid (7-amino-3-hydroxy-4'-flavonecarboxylic acid) is filtered, washed with water and dried by azetropy with benzene. Yield 54%. MP >260° C.

(b) Preparation of methyl 7-amino-3-hydroxy-4'-flavonecarboxylate

The mixture consisting of 4 g of the acid prepared above, 320 ml of methyl alcohol, 8 ml of methanesulfonic acid is heated to reflux of the methyl alcohol with stirring for 15 hours. The solvent is evaporated and the evaporation residue is washed with water. The methyl ester of the acid is filtered and dried by azeotropy with benzene. Yield 75%.

(c) Preparation of methyl 7-methanesulfonamido-3-methanesulfonyloxy-4'-flavonecarboxylate 2.5 g of methyl 7-amino-3-hydroxy-4'-flavonecarboxylate are put in suspension in 25 cc of anhydrous benzene. The mixture is cooled to 0° C., and 10 cc of methanesulfonic acid chloride are added drop by drop. The mixture is stirred at ambient temperature until the reaction is complete. The reaction is checked by thin-layer chromatography (benzene (90)-dioxane (25)-acetic acid (4) elution solvent). The mixture is poured into 300 cc of ice water. The precipitate is filtered, washed with water and dried. The resulting product is purified by open silica column chromatography. MP=250° C. NMR in DMSO(D6): δ=3.3 ppm, 3H, singlet, CH$_3$ methanesulfonamido; δ=3.6 ppm, 3H, singlet, CH$_3$ $_L$ $_{methanesulfonyloxy}$; δ=3.9 ppm, 3H singlet, CH$_3$ methyl ester; δ=7.1–8.4 ppm, 7H, complex multiplet, aromatic protons; δ=10.7 ppm, 1H, dome, NH; (interchangeable with D$_2$O).

EXAMPLE 3

7-Acetamido-3-acetoxy-4'-flavonecarboxylic acid (formula I product with R$_1$=OCOCH$_3$, R$_2$=NHCOCH$_3$; code name COR19 94) is prepared according to Example 2c by reaction of methyl 7-amino-3-hydroxy-4'-flavonecarboxylate with acetic acid chloride with saponification of the methyl ester as described in Example 1c.

MP >300° C. NMR in DMF(D7)+5 drops of DMSO(D6): δ=2.2 ppm, 3H singlet, CH$_3$; δ=2.4 ppm, 3H, singlet, CH$_3$; δ=7.3–8.4 ppm, 7H, complex multiplet, aromatic protons; δ=10.6 ppm, 1H, broad peak, NH, (interchangeable with D$_2$O); δ=12.5 ppm, 1H, very spread out peak, COOH, (interchangeable with D$_2$O).

EXAMPLE 4

Preparation of 7-acetamido-3-propyl-4'-flavonecarboxylic acid; formula I product with R$_1$=C$_3$H$_7$, R$_2$=NHCOCH$_3$; code name COR19 91

The mixture consisting of 49.5 g of N-acetyl-m-anisidine, 72.3 cc of valeric acid chloride and 200 cc of methylene chloride is cooled to 0° C. 120 g of aluminum chloride are added little by little. The reaction mixture is refluxed for 2 hours with stirring, cooled, then poured in ice water. The resulting oily product is extracted with chloroform. The chloroform phase in turn is extracted with 2N sodium hydroxide solution which is then acidified. Thus, 24 g of 5-acetamido-2-valeryl phenol (MP 113° C.) are obtained.

The mixture consisting of 23 g of the phenol obtained above, 23 g of paramethoxycarbonylbenzoic acid chloride, 94 g of anhydrous potassium carbonate, 1.7 liter of anhydrous acetone is refluxed for 8 hours with stirring. The reaction mixture is cooled. The inorganic salts are eliminated by filtering and the acetone phase is evaporated dry. The residue is recrystallized in the minimum of ethyl alcohol. Thus 7 g of 7-acetamido-3-propyl-4'-flavonecarboxylic acid methyl ester are obtained. MP=244° C. This ester is saponified by the technique described in example 1c to obtain acid COR19 91. MP >300° C. NMR in DMSO(D6) : δ=0.8 ppm, 3H, triplet, CH$_3$(propyl); δ=1.1–1.8 ppm, 2H, poorly resolved multiplet, CH$_2$CH$_2$CH$_3$; δ=2.0–2.7 ppm, 5H, complex multiplet, CH$_3$ (acetamido)+CH$_2$CH$_2$CH$_3$ (of which CH$_3$ at δ=2.1 ppm); δ=7.2–8.3 ppm, 7H, complex multiplet, aromatic protons; δ=10.4 ppm, 1H, broad peak, NH, (interchangeable with D$_2$O); δ=13.1 ppm, 1H, dome, COOH, (interchangeable with D$_2$O).

EXAMPLE 5

Preparation of 7-acetamido-3-ethyl-4'-flavonecarboxylic acid; formula I product with R$_1$=C$_2$H$_5$, R$_2$=NHCOCH$_3$, code name COR19 93

This product is prepared according to the method described in example 4. MP=292° C. NMR is DMSO(D6): δ=1.1 ppm, 3H, triplet, CH$_3$(ethyl); δ=2.0–2.7 ppm, 5H, complex multiplet, CH$_3$(acetamido)+CH$_2$ ( of which CH$_3$ at δ=2.1 ppm); δ=7.3–8.3 ppm, 7H, complex multiplet, aromatic protons; δ=10.6 ppm, 1H, broad peak, NH, (interchangeable with D$_2$O); δ=13.1 ppm, 1H, dome, COOH, (interchangeable with D$_2$O).

EXAMPLE 6

Preparation of 7-acetamido-3-propyl-4'-flavonecarboxylic acid piperidine amide; formula I product with R$_1$=C$_3$H$_7$, R$_2$=NHCOCH$_3$, piperidine amide; code name COR35 05

0.3 cc of SOCl$_2$ and 1 drop of dimethylformamide are added to 1 g of 7-acetamido-3-propyl-4'-flavonecarboxylic acid, prepared according to example 4, in 10 ml of dry dichloroethane. The mixture is refluxed for 3 hours 30 minutes then allowed to stand for 15 hours. The acid chloride is filtered and washed with dichloroethane. Yield 66%.

4 g of piperidine are added to 0.7 g of the acid chloride. The mixture is heated at 50°–60° C. with stirring for two hours, then poured in ice water. The amide is extracted with chloroform. The chloroform phase is washed with water, dried on sodium sulfate and evaporated. The residue is picked up in a little ethyl ether, filtered and dried. Yield 38%. MP=238° C. NMR in CDCl$_3$: δ=0.9 ppm, 3H triplet, CH$_3$(propyl); δ=1.3–2.0 ppm, 8H, complex multiplet, CH$_2$CH$_2$CH$_3$+3CH$_2$C of piperidine; δ=2.2 ppm, 3H, singlet, CH$_3$ (acetamido); δ=2.3–2.7 ppm, 2H, poorly resolved triplet, CH$_2$CH$_2$CH$_3$; δ=3.1–4.1 ppm, 4H, complex multiplet, CH$_2$N; δ=7.1–8.3 pm, 7H, complex multiplet, aromatic protons; δ=9.8 ppm, 1H, broad peak, NH, (interchangeable with D$_2$O).

EXAMPLE 7

Preparation of methyl 7-methanesulfonamido-3-propyl-4'-flavonecarboxylate; formula I product with R$_1$=C$_3$H$_7$, R$_2$=NHSO$_2$CH$_3$, methyl/ester; code name COR19 99

(a) Preparation of methyl 7-amino-3-propyl-4'-flavonecarboxylate 14 g of methyl 7-acetamido-3-propyl-4'-flavonecarboxylate, prepared according to example 4, are put in suspension in 700 cc of methyl alcohol. After addition of 300 cc of methyl alcohol saturated with gaseous hydrochloric acid, the mixture is heated at 100° C. with stirring for 2 hours. The methyl alcohol is evaporated and water is added to the residue. The methyl 7-amino-3-propyl-4'-flavonecarboxylate precipitates. The precipitate is filtered, washed with water until the washing waters are neutral. Thus 12 g of amino derivative are obtained.

(b) Preparation of methyl 7-methanesulfonamido-3-propyl-4'-flavonecarboxylate 3 g of amine thus prepared are dissolved in 15 cc of pyridine and 5 cc of mesityl chloride are added drop by drop. The stirring is maintained for 12 hours at ambient temperature, then the reaction mixture is poured into ice water. The resulting precipitate is filtered, washed and dried. Thus, 2 g of methyl 7-methane-3-propyl-4'-flavonecarboxylate are obtained. MP=235° C. NMR in DMSO(D6): $\delta=0.8$ ppm, 3H, triplet, $CH_3$(propyl); $\delta=1.1-1.8$ ppm, 2H, poorly resolved multiplet, $CH_2CH_2CH_3$; $\delta 2.2-2.6$ ppm, 2H, poorly resolved triplet, $CH_2CH_2CH_3$; $\delta=3.2$ ppm, 3H, singlet, $CH_3$(methanesulfonamido); $\delta=3.9$ ppm, 3H, singlet, $CH_3$ ester; $\delta=7.0-8.2$ ppm, 7H, complex multiplet, aromatic protons.

EXAMPLE 8

Preparation of 7-methanesulfonamido-3-propyl-4'-flavonecarboxylic acid; formula I product with $R_1=C_3H_7$, $R_2=NHSO_2CH_3$; code name COR35 01

2.7 g of methyl ester prepared according to example 7 are dissolved in 300 cc of dioxane. A solution of 4 g of sodium carbonate in 80 cc of water is added to this solution. The mixture is refluxed with stirring for 6 hours, then cooled and ice water is added. The insoluble material is filtered, then the filtrate is acidified with concentrated HCl. The precipitate is filtered, washed with water and dried. Thus, 2 g of acid are obtained. MP=272° C. NMR in DMSO(D6): $\delta=0.8$ ppm, 3H, triplet, $CH_3$(propyl); $\delta=1.1-1.8$ ppm, 2H, poorly resolved multiplet, $CH_2CH_2CH_3$; $\delta=2.1-2.7$ ppm, 2H, poorly resolved triplet, $CH_2CH_2CH_3$; $\delta=3.2$ ppm, 3H, singlet, $CH_3$(methanesulfonamido); $\delta=7.1-8.3$ ppm, 7H, complex multiplet, aromatic protons; $\delta=10.7$ ppm, 1H, dome, NH, (interchangeable with $D_2O$); $\delta=13.2$ ppm, 1H, dome, COOH, (interchangeable with $D_2O$).

EXAMPLE 9

Synthesis of methyl 7-(morpholinoacetamido)-3-propyl-4'-flavonecarboxylate.

Formula I product with $R_1=C_3H_7$,

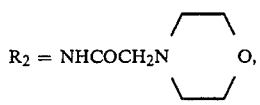

methyl ester; code name COR±17

8 cc of chloroacetyl chloride are added, with stirring, to a mixture consisting of 9.5 g of methyl 7-amino-3-propyl-4'-flavonecarboxylate made according to Example 7a, 1 liter of benzene and 9 g of anhydrous $K_2CO_3$. The mixture is heated to reflux of the benzene for 2 hours, then cooled. The benzene phase is washed with water. A precipitate is formed which is filtered and dissolved in chloroform. The benzene and chloroform phases are evaporated. Methyl 7-(2-chloracetamido)-3-propyl-4'-flavonecarboxylate is obtained with a yield of 80%. MP=162° C.

The mixture consisting of 9.2 of this derivative, 700 cc of benzene, 20 cc of morpholine is heated to reflux of the benzene with stirring for 4 hours, then cooled. The benzene phase is washed with water several times, dried on sodium sulfate and evaporated. The residue is recrystallized in ethyl alcohol. Yield 60%. MP=196° C. NMR in $CDCl_3$: $\delta=0.9$ ppm, 3H, triplet, $CH_3$(propyl), $\delta=1.2-1.9$ ppm, 2H, poorly resolved multiplet, $CH_2CH_2CH_3$; $\delta=2.3-2.9$ ppm, 6H, complex multiplet, $CH_2CH_2CH_3+2CH_2N$ (morpholine); $\delta=3.2$ ppm, 2H, singlet, $COCH_2N$; $\delta=4.0$ ppm, 3H, singlet, $CH_3$, ester; $\delta=7.0-8.3$ ppm, 7H, complex multiplet, aromatic protons; $\delta=9.4$ ppm, 1H, broad peak, NH, (interchangeable with $D_2O$).

EXAMPLE 10

Synthesis of 7-morpholinoacetamido-3-propyl-4'-flavonecarboxylic acid hydrochloride Formula I product with $R=C_3H_7$,

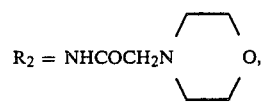

hydrochloride; code name COR 35 02.

2 g of sodium carbonate dissolved in 60 cc of water are added to 2 g of methyl ester prepared according to example 9 and dissolved in 250 cc of ethyl alcohol and 125 cc of dioxane. The mixture is kept at reflux with vigorous stirring until complete saponification, then cooled and neturalized with acetic acid. The precipitate is filtered and recrystallized in ethyl alcohol. The product is dissolved in methyl alcohol; a few ml of methyl alcohol saturated with gaseous HCl, then ethyl ether are added to make the COR 3502 precipitate. The precipitate is filtered and washed with ethyl ether. Yield 40%. NMR in DMSO(D6): $\delta=0.8$ ppm, 3H, poorly resolved triplet, $CH_3$(propyl); $\delta=1.1-1.8$ ppm, 2H, poorly resolved multiplet, $CH_2CH_2CH_3$; $\delta=2.1-2.7$ ppm, 2H, poorly resolved triplet, $CH_2CH_2CH_3$; $\delta=3.1-4.7$ ppm, 10H, complex multiplet, $NCH_2+OCH_2$; $\delta=7.4-8.3$ ppm, 7H, complex multiplet, aromatic protons; $\delta=9-13$ ppm, 3H, very spread out peak, $NH+NH^++COOH$, (interchangeable with $D_2O$).

EXAMPLE 11

Preparation of 7-piperidinoacetamido-3-propyl-4'-flavonecarboxylic acid hydrochloride Formula I product with $R_1=C_3H_7$,

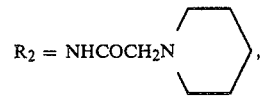

hydrochloride; code name COR 19 95.

COR 19 95 is prepared according to the techniques described in examples 9 and 10. MP=179° C. NMR in DMF(D7): $\delta=0.8$ ppm, 3H, triplet, $CH_3$(propyl); $\delta=1.2-2.7$ ppm, 10H, complex multiplet, $5CH_2C$; $\delta=3.1-3.8$ ppm, 4H, complex multiplet, $2N-CH_2$(piperidine); $\delta=4.4$ ppm, 2H, singlet, $NCH_2CO$; $\delta=7.4-8.4$ ppm, 7H, complex multiplet, aromatic protons; $\delta=12.1$ and 6-10 ppm, 3H, broad peak and spread out peak, $NH+NH^++COOH$, (interchangeable with $D_2O$).

EXAMPLE 12

Preparation of methyl N,N-7-dimethylsulfamoyl-3-propyl-4'-flavonecarboxylate, formula I product with $R_1=C_3H_7$, $R_2=SO_2N(CH_3)_2$; methyl ester; code name COR 35 08

(a) Preparation of methyl 7-chlorosulfonyl-3-propyl-4'-flavonecarboxylate 6 g of methyl 7-amino-3-propyl-4'-flavonecarboxylate are put in suspension with stirring in 120 cc of acetic acid. 18 cc of concentrated hydrochloric acid are added in 5–10 min, then a solution of 4.5 g of sodium nitrite in 6 cc of water are added drop by drop with the reaction tremperature being kept at 5° C. The mixture is kept at ambient temperature for 20 min then poured by fractions in an iced solution of 800 cc of acetic acid saturated with $SO_2$ (solution to which 4 g of $CuCl_2.2H_2O$ dissolved in 8 cc of water has been added). Stirring is maintained at ambient temperature for 2 hours, then 400 cc of ice water are added. The resulting precipitate is filtered, washed and dried. Thus, 4.8 g of methyl 7-chlorosulfonyl-3-propyl-4'-flavonecarboxylate are obtained. MP=128° C.

(b) Preparation of methyl N,N-7-dimethylsulfamoyl-3-propyl-4'-flavonecarboxylate.

1.2 g of 7-chlorosulfonyl derivative are dissolved in 100 cc of benzene. After addition of 10 cc of dimethylamine, the mixture is brought to reflux and maintained for two hours with stirring. After cooling, 100 cc of ethyl ether are added and the organic phase is washed with water. This phase is then dried on sodium sulfate and evaporated. The resulting solid residue is recrystallized in ethyl alcohol. Thus 0.7 g of COR 35 08 are obtained; MP=166° C. NMR in $CDCl_3$: $\delta=0.9$ ppm, 3H, triplet, $CH_3$(propyl); $\delta=1.2$–1.9 ppm, 2H, poorly resolved multiplet, $CH_2CH_2C_3$; $\delta=2.4$–2.7 ppm, 2H, poorly resolved triplet, $CH_2CH_2CH_3$; $\delta=2.8$ ppm, 6H, singlet, $NCH_3$; $\delta=4.0$ ppm, 3H, singlet, $CH_3$ ester; $\delta=7.6$–8.6 ppm, 7H, complex multiplet, aromatic protons.

EXAMPLE 13

Preparation of N,N-7-dimethylsulfamoyl-3-propyl-4'-flavonecarboxylic acid; formula I product with $R_1=C_3H_7$, $R_2=SO_2N(CH_3)_2$; code name COR 35 09

2 g of ethyl ester prepared according to example 12 are dissolved in 100 cc of dioxane, then a solution of 2 g of sodium carbonate dissolved in 40 cc of water is added. The mixture is kept at reflux with stirring for 5 hours then cooled and 30 cc of ice water are added. The insoluble material is filtered, the filtrate is acidified with concentrated HCl then the resulting precipitate is filtered and dried. Thus 1 g of COR35 09 is obtained. MP=271° C. NMR in DMSO(D6); $\delta=0.8$ ppm, 3H, triplet, $CH_3$(propyl); $\delta=1.1$–1.8 ppm, 2H, poorly resolved triplet, $CH_2CH_2CH_3$; $\delta=2.2$–2.6 ppm, 2H, poorly resolved triplet, $CH_2CH_2CH_3$; $\delta=2.7$ ppm, 6H, singlet, $NCH_3$; $\delta=7.7$–8.4 ppm, 7H, complex multiplet, aromatic protons; $\delta=13.3$ ppm, 1H, dome, COOH, (interchangeable with $D_2O$).

EXAMPLE 14

Preparation of methyl N-7-methylsulfamoyl-3-propyl-4'-flavonecarboxylate; formula I product with $R_1=C_3H_7$, $R_2=SO_2NHCH_3$, methyl ester; code name COR35 10

This product is prepared according to Example 12b from methyl 7-chlorosulfonyl-3-propyl-4'-flavonecarboxylate and methylamine. MP=134° C. NMR in $CDCl_3$; $\delta=0.9$ ppm, 3H, triplet; $CH_3$(propyl); $\delta=1.2$–1.9 ppm, 2H, poorly resolved multiplet, $CH_2CH_2CH_3$; $\delta=2.3$–2.6 ppm, 2H, poorly resolved triplet, $CH_2CH_2CH_3$; $\delta=2.8$ ppm, 3H, doublet, $NCH_3$; $\delta=4.0$ ppm, 3H, singlet, $CH_3$ ester; $\delta=5.5$ ppm, 1H, quadruplet, NH (interchangeable with $D_2O$); $\delta=7.7$–8.5 ppm, 7H, complex multiplet, aromatic protons.

EXAMPLE 15

Preparation of N-7-methylsulfamoyl-3-propyl-4'-flavonecarboxylic acid; formula I product with $R_1=C_3H_7$; $R_2=SO_2NHCH_3$; code name COR35 11

This product is prepared by saponification according to example 13 of the methyl ester obtained according to example 14. MP=261° C. NMR in DMF(D7): $\delta=0.9$ ppm, 3H, triplet, $CH_3$(propyl); $\delta=1.2$–2.0 ppm, 2H, poorly resolved multiplet, $CH_2CH_2CH_3$; $\delta=2.3$–2.9 ppm, 5H, complex multiplet, $CH_2CH_2CH_3+NCH_3$; $\delta=7.7$–8.5 ppm, 7H, complex multiplet, aromatic protons; $\delta=7$–10 ppm, 2H, very spread out peak, NH+COOH, (interchangeable with $D_2O$).

EXAMPLE 16

Preparation of 7-(N-hydroxyethyl N-methyl sulfamoyl)-3-propyl-4'-flavonecarboxylic acid; formula I product with $R_1=C_3H_7$, $R_2=SO_2NCH_3CH_2CH_2OH$; code name COR35 19

The methyl ester of this acid is prepared from methyl 7-chlorosulfonyl-3-propyl-4'-flavonecarboxylate and 2-(methylamino) ethyl alcohol according to Example 12b; MP=90°–95° C. The acid is prepared from this ester by saponification according to example 13.

MP=191° C. NMR in DMF(D7): $\delta=0.9$ ppm, 3H, triplet, $CH_3$(propyl); $\delta 1.1$–2.0 ppm; 2H, poorly resolved multiplet, $CH_2CH_2CH_3$; $\delta=2.3$–2.7 ppm, 2H, poorly resolved triplet, $CH_2CH_2CH_3$; $\delta=3.0$ ppm, 3H, singlet, $NCH_3$; $\delta=3.3$ ppm, 2H, triplet, $NCH_2$; $\delta=3.7$ ppm, 2H, triplet, $CH_2O$; $\delta=7.7$–8.4 ppm, 7H, complex multiplet, aromatic protons; $\delta=5$–10 ppm, 2H, very spread out peak, OH+COOH, (interchangeable with $D_2O$).

EXAMPLE 17

Preparation of 7-sulfamoyl-3-propyl-4'-flavonecarboxylic acid; formula I product with $R_1=C_3H_7$, $R_2=SO_2NH_2$; code name of COR35 22

5 g of methyl 7-chlorosulfonyl-3-propyl-4'-flavonecarboxylate prepared according to Example 12a are dissolved in 300 cc of benzene. An ammonia current is made to pass in the solution for 10 min. The precipitate is filtered and washed with benzene. Yield 68%.

3.2 g of methyl 7-sulfamoyl-3-propyl-4'-flavonecarboxylate thus prepared are dissolved in 200 cc of dioxane. 3 g of sodium carbonate dissolved in 150 cc of water are added. The mixture is stirred vigorously for 4 hours with reflux of the dioxane. Thin-layer chromatography is used to verify that the reaction is complete. Ice water is added to the cooled mixture and it is filtered on creped paper. The mixture is acidified. The precipitate is filtered then dissolved in boiling ethyl alcohol. The solution is filtered on a millipore filter and the filtrate is concentrated to make the acid reprecipitate which is filtered after cooling. Yield 55%. MP=287° C. NMR in DMSO($D_6$): $\delta=0.8$ ppm, 3H, triplet, $CH_3$(propyl); $\delta=1.1-1.9$ ppm, 2H, poorly resolved multiplet, $CH_2CH_2CH_3$; $\delta=2.2-2.7$ ppm, 2H, poorly resolved triplet, $CH_2CH_2CH_3$; $\delta=7.5-8.4$ ppm, 9H, complex multiplet, $NH_2$=aromatic protons; $\delta=13.3$ ppm, 1H, dome, COOH, (interchangeable with $D_2O$).

EXAMPLE 18

Preparation of 7-(piperidinoacetamido)-4'-flavonecarboxylic acid hydrochloride

Formula I product with $R_1=H$,

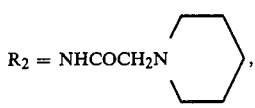

$R_2 = NHCOCH_2N$ , hydrochloride; code name COR35 03.

The methyl ester of this acid is prepared from methyl 7-amino-4'-flavonecarboxylate, according to example 9, then saponified and transformed into hydrochloride according to example 10. MP=299° C.

The pharmacological properties of the products, which are the object of this invention, are set forth below.

The advantage of the products of this invention in the treatment and prophylaxis of complications from diabetes has been shown in vitro by determination of the inhibiting activity of aldose reductase and in vivo in the neuropathy models induced by streptozotocin and in the cataract models induced by galactose.

INHIBITION OF ALDOSE REDUCTASE IN VITRO

The enzyme is extracted from beef crystalline lens by the method described by Hayman S. and Kinoshita J. H. (J. Biol Chem., 1965, 240, 2,877). The percentage of inhibition of the capacity of the enzyme to reduce glyceraldehyde to glycerol under the effect of the product to be tested is determined by the spectrophotometric determination of the amount of NADPH reacting according to the method described by Hayman and Kinoshita. We give below in parentheses after each product the value of the log 1/CI50 where CI50 represents the concentration expressed in mole/l resulting in 50% inhibition of the enzymatic activity: COR 19 85 (4.9); COR 19 91 (5.5); COR 19 93 (5.1); COR 19 94 (5.2); COR 19 99 (5.4); COR 35 01 (6.9); COR 35 02 (5.15); COR 35 07 (6.3); COR 35 09 (5.7); COR 35 11 (5.9); COR 35 19 (5.8); COR 35 22 (5.2).

NEUROPATHY WITH STREPTOZOTOCIN

Four batches of 10 rats weighing about 200 g were treated from D−2 to D+3 with a gummy julep of the product to be tested. On D 0 the animals received an i.p. injection of 100 mg/kg of streptozotocin dissolved in a citrate buffer. The glycemia of the rats was determined 24 hours and 3 days after injection of the streptozotocin and the sciatic nerves were removed to determine the sorbitol and inositol levels. Tested under these conditions, COR35 01, in a dose of 100 mg/kg/d, resulted in a reduction of the sorbitol level (level of 0.983±0.334 mg/kg/ in the control animals and 0.426±0.171 in the treated animals) and of inositol (level equal to 1.6555±0.372 mg/kg in the control animals and 1.184±0.340 in treated animals) in the sciatic nerves. COR 35 01 had no effect on the glycemia of the animals. The latter had a value of 4.03±0.89 (D1) and 5.44±0.90 (D2) in the control animals and 4.07±1.03 (D1) and 6.30+0.97 (D2) in the animals treated.

GALACTOSE CATARACTS

Rats, 14 days old, were kept in a cage of 11 with a mother for 3 days. From the 4th to the 9th day, the animals received the product to be tested or the reference product. At the end of pretreatment, the mothers were removed. Two out of the 11 animals were eliminated to obtain batches of homogenous weight. The selected rats were divided 3 by 3 into cages at random, and the diet containing 20% galactose was put in place. For 14 days, their crystalline lenses were observed with an ophthalmscope. The degree of cataract was evaluated by a marking system from 0 to 3.

The marks given to the treated animals were compared with those of the control animals by the Mann and Whitney U test (D. Schwartz, "Statistical Methods for the Use of Physicians and Biologists," Ed. Flammarion, Paris, 1963). The results are given in the table below.

The toxicity of the products of this invention was determined in mice. Thus, the $LD_0$ of COR19 91, of COR19 94 and of COR35 01 were more than 2000 mg/kg orally. COR35 17 caused 10% mortality after oral administration of a dose of 1000 mg/kg. Intraperitoneally COR35 01 did not cause any mortality at 250 mg/kg and caused 20% mortality at 500 mg/kg.

Besides their advantage in curative and preventive therapy of complications from diabetes, the products, which are the object of this invention, are also useful as diuretics. Thus, product COR35 07, tested in rats according to the method of Lipschitz et coll.(J. Pharm. Exp. Therap., 1943, 79, 97–110), results in an increase in urinary excretion of sodium (natruria was multiplied by 2.6 after oral administration of 20 mg/kg).

Considering their properties, along with a slight toxicity, the products according to this invention, are useful in human and veterinary therapy, for example, in the treatment and prevention of metabolic and, in particular, diabetic cataracts, in the treatment and prevention of diabetic neuropathies, in the treatment of edema and hydrosodium retentions, in the treatment of arterial hypertension. The products, which are the object of this invention, can be used alone or associated with antihypertensive or antidiabetic agents. They can be administered, associated with suitable vehicles or excipients, orally in the form of sugar-coated pills, tablets, syrup, drinkable ampoules, rectally in the form of suppositories, parenterally by cutaneous, intramuscular, intravenous injections, topically in the form of ointments or gels. They can also be put into compositions for ophthalmic use in the form of collyria or ointments. The doses administered will vary according to indication and patient from 5 to 500 mg/d in 2 to 6 doses orally, from 5 to 500 mg/d in 1 or 2 doses rectally, from 0.5 to 50 mg by parenteral injection.

| Treatment | GALACTOSE CATARACT AVERAGE INDEX | | | | | | | | | | | | |
|---|---|---|---|---|---|---|---|---|---|---|---|---|---|
| | D + 1 | D + 2 | D + 3 | D + 4 | D + 5 | D + 6 | D + 7 | D + 8 | D + 9 | D + 10 | D + 11 | D + 12 | D + 13 |
| Control gum | 0.0 ± 0.00 | 0.0 ± 0.0 | 0.41 ± 0.38 | 1.13 ± 0.44 | 1.88 ± 0.64 | 2.75 ± 0.46 | 2.81 ± 0.37 | 2.75 ± 0.38 | 2.81 ± 0.26 | 2.75 ± 0.38 | 2.63 ± 0.44 | 2.63 ± 0.35 | 2.19 ± 0.46 |
| COR35 09 100 mg/kg d | 0.0 ± 0.00 | 0.0 ± 0.0 | 0.031 ± 0.09 | 0.47 ± 0.34 S | 0.97 ± 0.43 S | 1.44 ± 0.62 S | 1.69 ± 0.65 S | 1.81 ± 0.59 S | 2.06 ± 0.73 S | 1.88 ± 0.69 S | 1.69 ± 0.53 S | 1.81 ± 0.37 S | 1.50 ± 0.46 S |

What is claimed as new and desired to be secured by Letters Patents of the United States is:

1. A compound of the formula

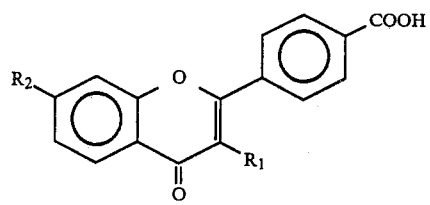

wherein $R_1$ is H, OH, $OCOCH_3$, $OCO_2CH_3$, branched or unbranched alkyl containing 1 to 5 carbon atoms, $R_2$ is $NHCOR_3$, $NHCOCH_2X$, $NHSO_2CH_3$, $N(SO_2CH_3)_2$, $SO_2N(CH_3)_2$, $SO_2NHCH_3$, $SO_2NCH_3CH_2CH_2OH$, $SO_2NH_2$, wherein $R_3$ is a lower alkyl containing 1 to 4 carbon atoms, and X is $NR_4R_5$ or

wherein $R_4$ and $R_5$ are both independently lower alkyls containing 1 to 4 carbon atoms and

is piperidine, pyrrolidine or morpholine, and pharmaceutically acceptable derivatives thereof such as esters, amides or salts.

2. The compound of claim 1, wherein said pharmaceutically acceptable derivatives thereof comprise ester, amide, alkali or alkaline-metal salt, and organic base derivatives of the carboxylic acid function.

3. The compound of claim 1, wherein said pharmaceutically acceptable salt derivatives thereof are acid addition salts of the compound.

4. A pharmaceutical composition suitable for human or veterinary use in the treatment of diabetes comprising the compound of claim 1 and a pharmaceutically acceptable carrier, wherein said compound is present in an anti-diabetic effective amount or an anti-diuretic effective amount.

5. The composition of claim 4, wherein said compound is present in an anti-diabetic effective amount.

6. The composition of claim 4, wherein said compound is present in an anti-diuretic effective amount.

* * * * *